United States Patent [19]

Domaas

[11] Patent Number: 5,071,346
[45] Date of Patent: Dec. 10, 1991

[54] DENTAL BURR STORAGE SYSTEM

[76] Inventor: David E. Domaas, 15910 46th Ave. N., Plymouth, Minn. 55446

[21] Appl. No.: 607,510

[22] Filed: Nov. 1, 1990

[51] Int. Cl.$^5$ .............................................. A61G 15/00
[52] U.S. Cl. ....................................... 433/77; 206/369; 206/379; 422/300
[58] Field of Search ................. 433/72, 77, 163, 165; 206/368, 369, 379; 422/300, 301, 310

[56] References Cited

U.S. PATENT DOCUMENTS

| | | | |
|---|---|---|---|
| 1,135,625 | 4/1915 | Savin | 433/77 |
| 3,092,443 | 6/1963 | Dietz | 433/77 |
| 3,248,167 | 4/1966 | Friedman | 206/369 |
| 4,050,894 | 9/1977 | Genis | 206/369 |
| 4,306,862 | 12/1981 | Knox | 433/77 |
| 4,327,060 | 4/1982 | Nisii | 422/300 |
| 5,006,066 | 4/1991 | Rouse | 433/77 |
| 5,022,858 | 6/1991 | Castellini | 433/77 |

FOREIGN PATENT DOCUMENTS

| | | | |
|---|---|---|---|
| 2950945 | 6/1981 | Fed. Rep. of Germany | 433/77 |
| 3143902 | 5/1983 | Fed. Rep. of Germany | 433/97 |
| 837613 | 2/1939 | France | 433/77 |
| 2577414 | 8/1986 | France | 433/77 |

Primary Examiner—Gene Mancene
Assistant Examiner—Michael Lynch
Attorney, Agent, or Firm—Hugh D. Jaeger

[57] ABSTRACT

A dental burr storage system for storing of dental burrs in a polymer, such as a polysulfone structure for storage as well as for sterilization. With the concern over AIDS, patients are now requiring dentists to store their personal dental burrs in their own storage container. The container provides for storage of the dental burrs, as well as sterilization of the dental burrs. The storage system includes a dental burr base and a dental burr cap, which threads onto the base in either a storage position for the dental burrs or a support position for the dental burrs. The base includes a plurality of holes on a cylindrical member for passage of gases during sterilization procedures. A threaded cap also includes a plurality of holes for passage of gases during a sterilization procedure.

5 Claims, 9 Drawing Sheets

5,071,346

DENTAL BURR STORAGE SYSTEM

BACKGROUND TO THE INVENTION

1. Field of the Invention

The present invention pertains to dentistry, and more particularly, pertains to a dental burr storage system for storage and sterilization of dental burrs.

2. Description of the Prior Art

A current concern of dental patients is the use of dental burrs and maintaining sterilization of those dental burrs. With a concern over AIDS and infection control, dentists are concerned with protection for their patients, their staff, and themselves.

One problem has been the storage and sterilization of these dental burrs in that the dental burrs have traditionally been stored in the dentist's operatory and wiped off with alcohol or disinfecting solution before use on the next patient. Alternatively, some dentists use a magnetic block to which burrs are attached, and need to be placed in a sterilization bag so that burrs are not lost in the autoclave.

The present invention overcomes the disadvantages of the prior art problems. The dental burrs can be stored in an individualized storage container for sterilization in the individualized storage container, where each of the dental burrs are designated and stored for the next patient.

SUMMARY OF THE INVENTION

The general purpose of the present invention is a dental burr storage system providing a base for the support of dental burrs and a cap for screwing onto the base in either a storage position or a sterilization position.

According to one embodiment of the present invention, there is provided a dental burr storage system, including a cylindrical member with threads on each end and a rim therebetween, a plurality of holes extending through the cylindrical member, an inner circular recess area in the bottom of the cylindrical member for gas passage, as well as support of dental burrs, a threaded round cover including inner threads for threaded engagement with each end of the cylindrical member for either storage of the dental burrs or support of the dental burrs in the cylindrical member, and a plurality of gas passage holes for sterilization.

Significant aspects and features of the present invention include a dental burr storage system which stores dental burrs for either use by a dentist or for sterilization in the dental office by the dentist.

Other significant aspects and features of the present invention include a dental burr storage system, which is a small container which provides for placing of the burrs from operatory into the container, then for subsequent cleaning in an ultrasonic cleaner, and then for subsequent sterilizing in the autoclave. The system is compact and prevents loss of the dental burrs throughout the cleaning and sterilizing procedures where the dental burrs and the container can then be utilized in another procedure as so desired. In addition, this storage system provides enough holes for burrs most dentists would be interested in using.

Other significant aspects and features of the present invention include a small size which easily fits on a bracket table. The dental burr storage system can be color coded for specific procedures. The dental burr storage system can be stacked and more easily stored than the burr caddy. This is important for dentists who do not autoclave dental instruments and dental burrs in the same autoclave bag. The cover helps prevent dust or debris from getting on the burrs during storage, an advantage over the prior art. Short shank burrs will not fall out of the dental burr storage system. The shape is one traditionally accepted by dentists and can fit more burrs than the prior art. The dental burr storage system can easily be placed in the ultrasonic followed by steam autoclaving. The dental burr storage system is made of a durable autoclavable plastic which holds up well in today's ultrasonic solutions.

Having thus described the preferred embodiments of the present invention, it is a principal object hereof to provide a convenient dental burr storage system for sterilization of the dental burrs and for use of the dental burrs.

One object of the present invention is to store, sterilize and provide for the use of dental burrs in a convenient delivery system and without loss of the dental burrs.

Another object of the present invention is to enhance infection control objectives in the dental office.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
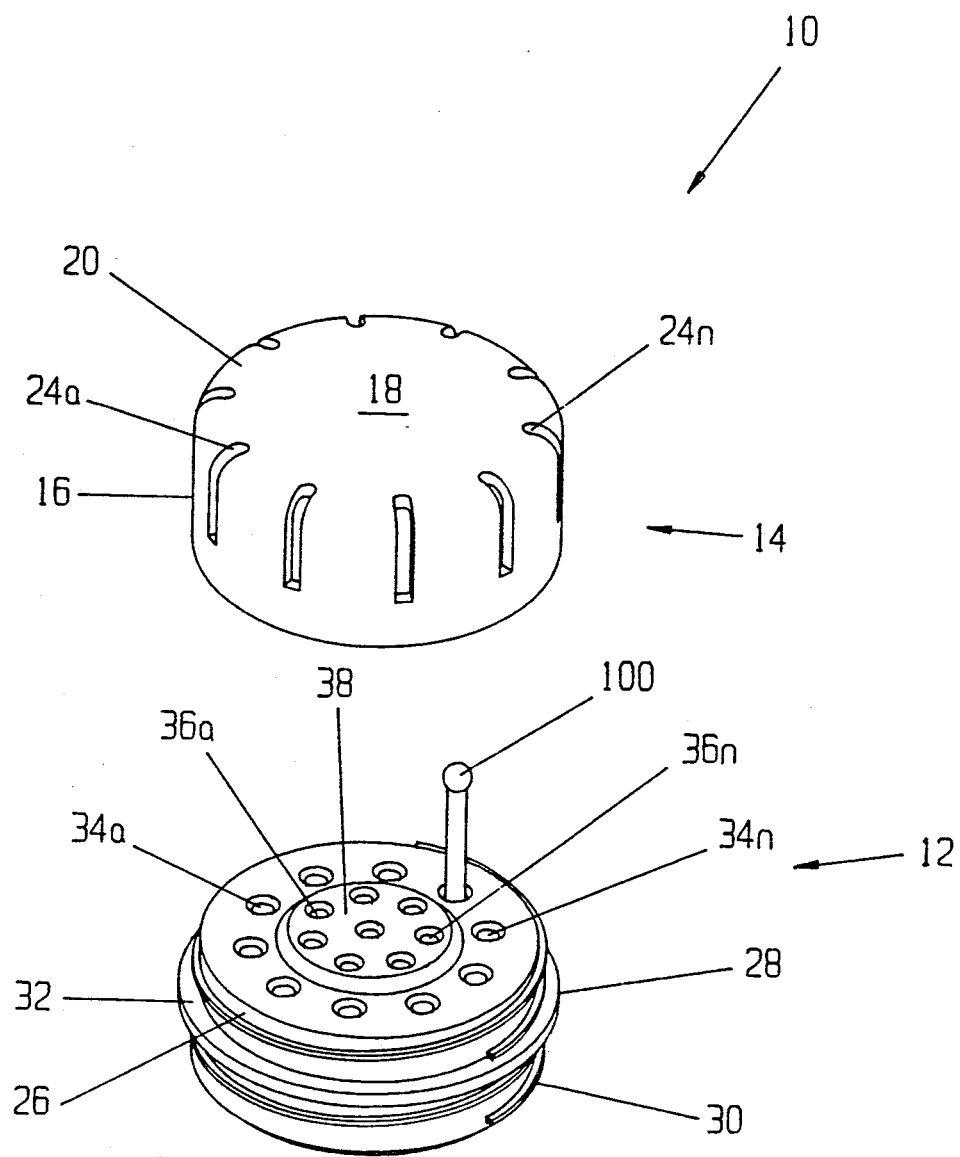
FIG. 1 illustrates a top perspective view of a dental burr storage system components separated including a cap and a base, the present invention.
Figure 6:
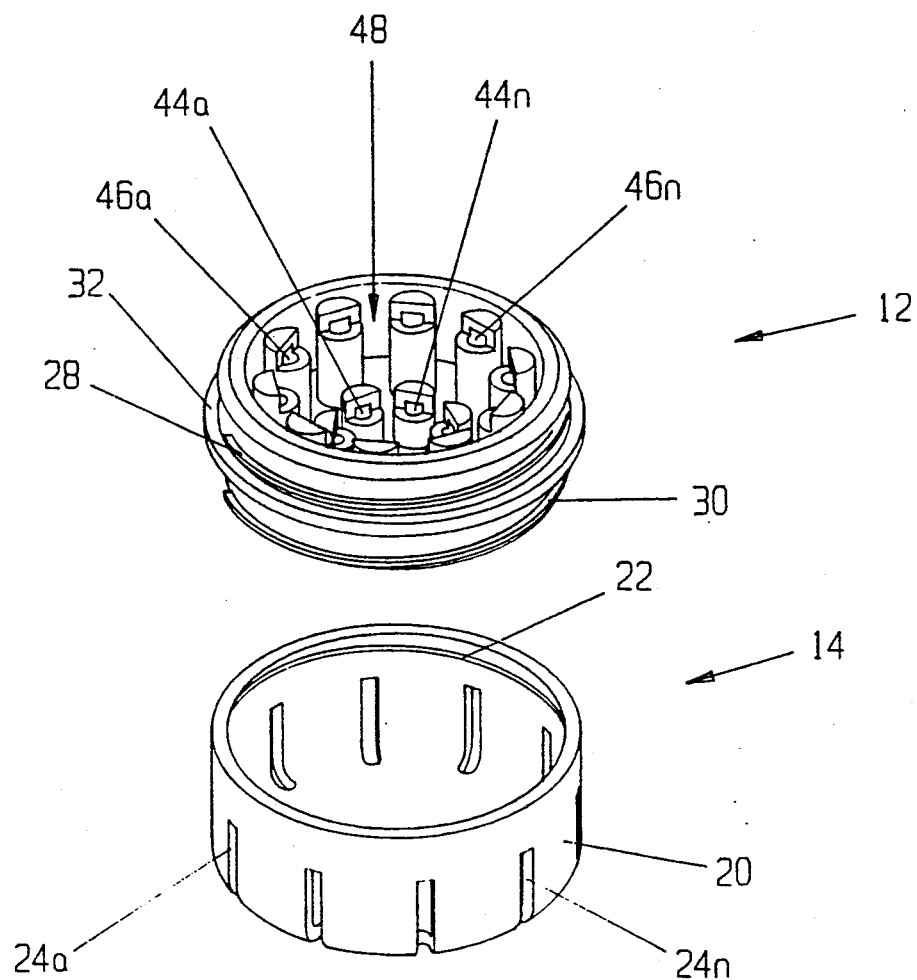
FIG. 6 illustrates a bottom perspective view of the dental burr storage system components separated including the cap and the base.

FIG. 1 illustrates a top perspective view of the dental burr storage system 10 components separated including a base 12 and a cap 14. The cap 14 includes a side 16, a top 18, a rounded edge member 20 therebetween, inner threads 22, and a plurality of elongated slots 24a-24n spaced about the side 16 and the top 18 as illustrated in FIGS. 2, 3, 4 and 6 for purposes of gases for sterilizing. The outer diameter of the cap is about 2 inches by way of example and for purposes of illustration only, and not to be construed as limiting of the present invention. The base 12 includes a cylindrical member 26, upper and lower threaded ends 28 and 30, a rim 32 and a plurality of inner and outer beveled holes 34a-34n and 36a-36n respectively extending through the cylindrical member 26. A raised portion 38 accommodates the inner holes 36a-36n to offset the inner dental burrs at a higher position with respect to the outer dental burrs. Inner and outer beveled holes 34a-34n and 36a-36n support the dental burrs and include gas passage ports 44a-44n and 46a-46n on the opposing side of the base 12 as illustrated in FIG. 6. The dental burrs fit loosely in the holes 34a-34n and 36a-36n to allow gas to flow from the ports 44a-44n and 46a-46n.

Figure 2:
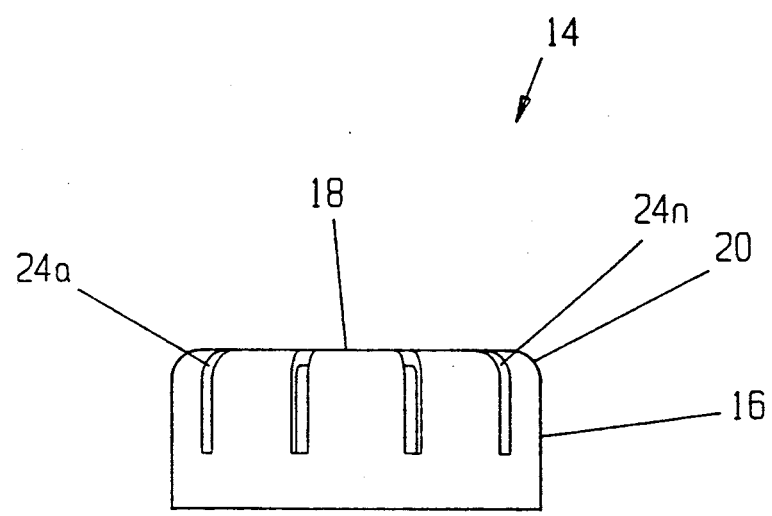
FIG. 2 illustrates a side view of the cap.

FIG. 2 illustrates a side view of the cap 14 where all numerals correspond to those elements previously described.

Figure 3:
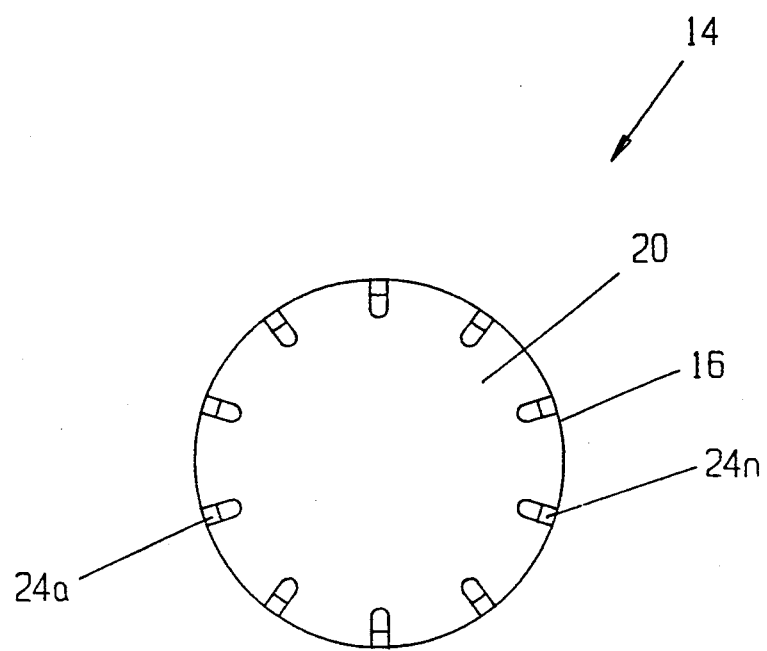
FIG. 3 illustrates a top view of the cap.

FIG. 3 illustrates a top view of the cap 14 where all numerals correspond to those elements previously described.

Figure 4:
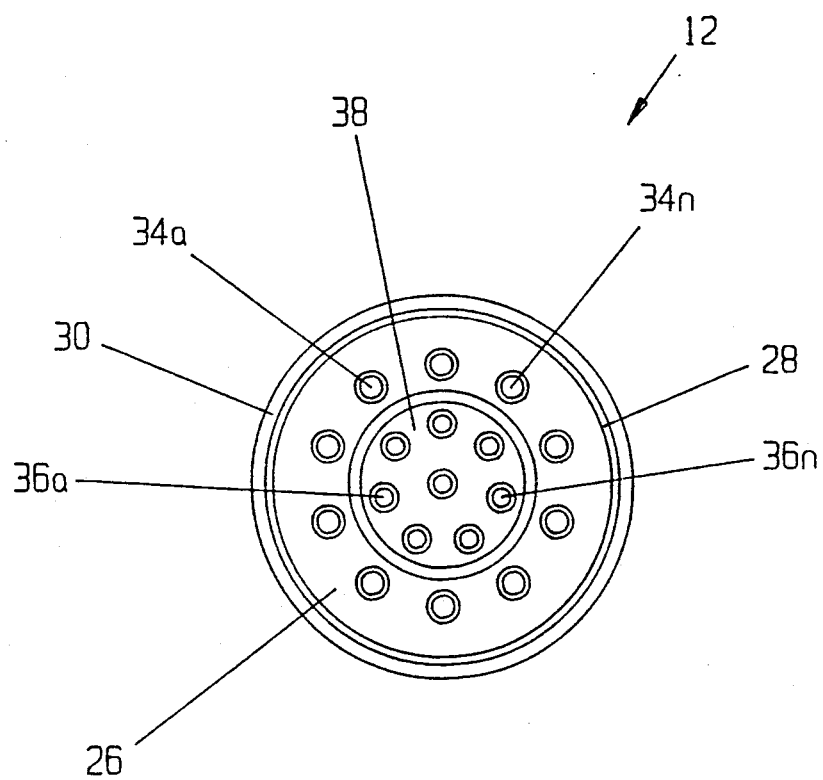
FIG. 4 illustrates a top view of the base.

FIG. 4 illustrates a top view of the base 12 where all numerals correspond to those elements previously described.

Figure 5:
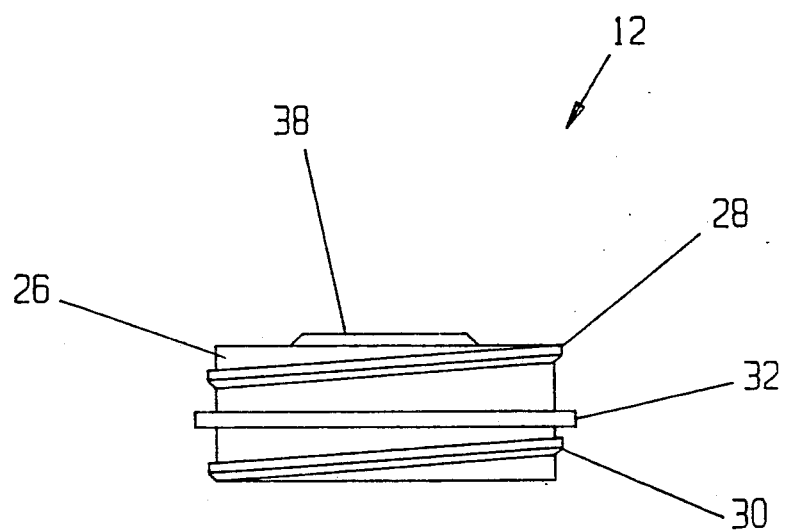
FIG. 5 illustrates a side view of the base.

FIG. 5 illustrates a side view of the base 12 where all numerals correspond to those elements previously described.

FIG. 6 illustrates a bottom perspective view of the dental burr storage system 10 component separated including the cap 14 and the base 12 where all numerals correspond to those elements previously described. An open area 48 is provided either by injection molding or by a milling process for passage of sterilizing gases into the ports 44a-44n and 46a-46n.

Figure 7:
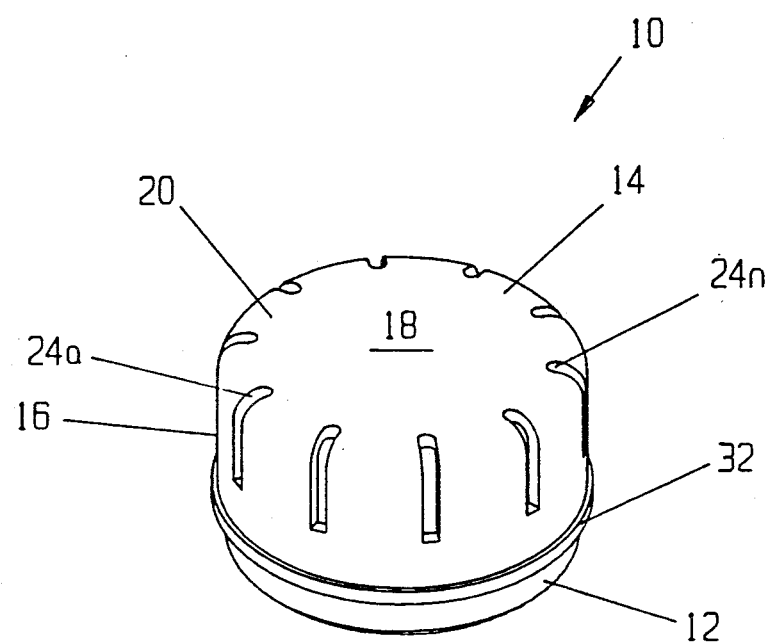
FIG. 7 illustrates a top perspective view of the dental burr storage system.

FIG. 7 illustrates a top perspective view of the dental burr storage system 10 where the base 12 and the cap 14 are mutually engaged where all numerals correspond to those elements previously described.

Figure 8:
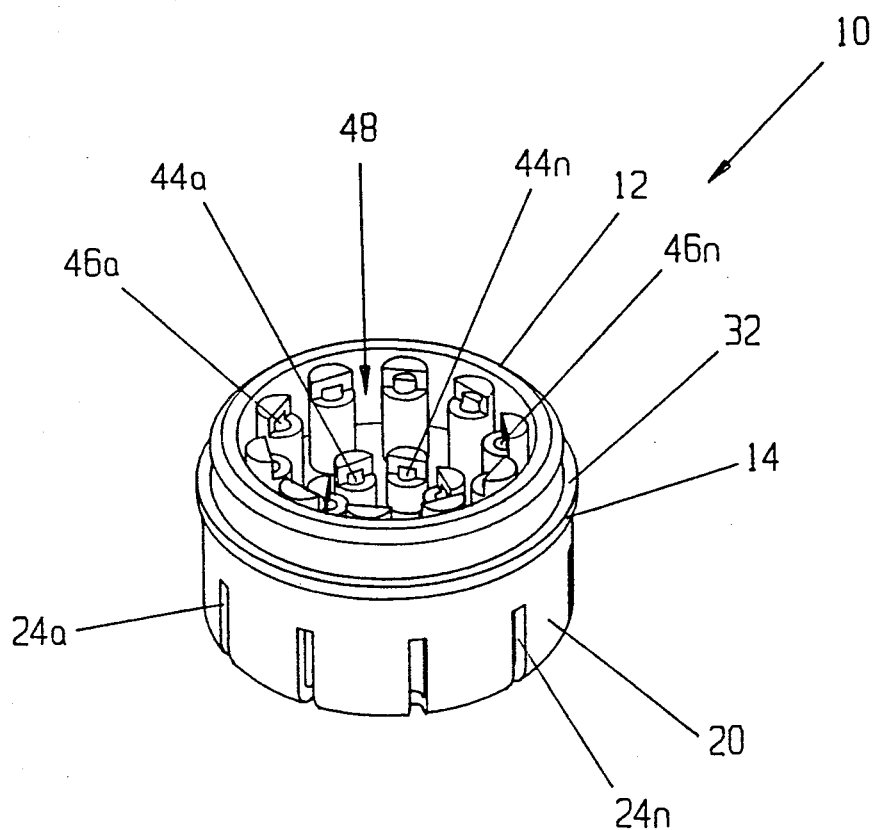
FIG. 8 illustrates a bottom perspective view of the dental burr storage system; and, FIG. 9 illustrates a top perspective view of the dental burr storage system with the base supporting a representative dental burr.

FIG. 8 illustrates a bottom perspective view of the dental burr storage system 10 where the base 12 and the cap 14 are mutually engaged where all numerals correspond to those elements previously described.

Figure 9:
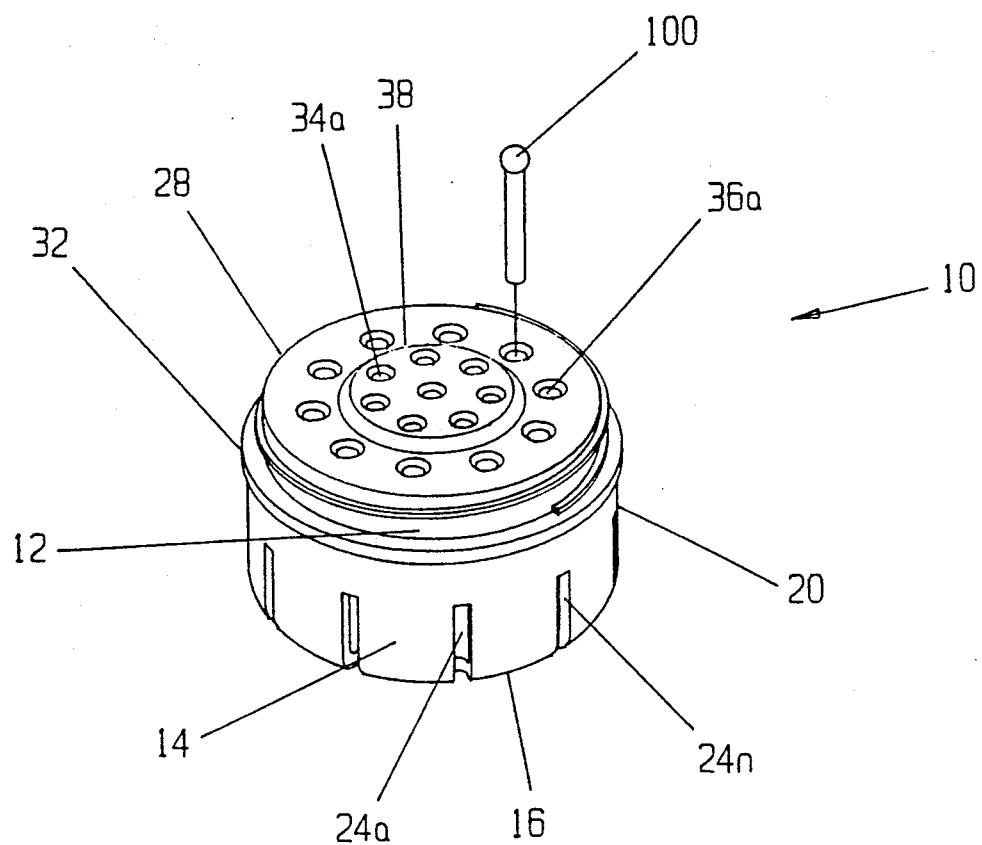

FIG. 9 illustrates a top perspective view of the dental burr storage system 10 with the base 12 supporting a representative dental burr 100 where all numerals correspond to those elements previously described.

MODE OF OPERATION

The dental burrs are stored in the dental burr storage system as illustrated in FIG. 7, and can also be sterilized in either configuration of the dental burr storage system of FIG. 7 or FIG. 9, but preferably in a storage position as in FIG. 7.

The dental burr storage system is user friendly, particularly for the dentist or the dental assistant, and easily fits within the palm of an individual's hand, especially when the cap is screwed into the base in a storage or sterilizing position as illustrated in FIG. 7.

In dental operations, the cap is unscrewed from the base's top and rescrewed onto the base's bottom. The dentist then has easy access to each of the dental burrs as supported in the base.

Various modifications can be made to the present invention without departing from the apparent scope hereof. Other suitable polymer materials can be utilized besides polysulfone. The teachings of the present invention can also be applied to a square base structure with a frictionally engaging a slip on cap.

I claim:

1. Dental burr storage system for supporting dental burrs comprising:
    a. a support means including engagement surfaces on each end and a rim therebetween;
    b. a plurality of holes extending through said support means;
    c. means encompassing each of said holes for supporting a lower portion of the dental burrs and means for passage of sterilization gases; and,
    d. a cover including a plurality of gas passage means and means for frictional engagement with either end of said support means.

2. Dental burr storage system of claim for infection control.

3. Dental burr storage system for supporting dental burrs comprising:
    a. a cylindrical member including threads on each end and a rim therebetween;
    b. a plurality of holes extending through said cylindrical member;
    c. means encompassing each of said holes for supporting a lower portion of the dental burrs and means for passage of sterilization gases; and,
    d. a threaded round cover including inner threads and a plurality of gas passage means and means for threaded engagement with either end of said cylindrical member.

4. Process for sterilizing of dental burrs for infection comprising the steps of:
    a. placing at least one dental burr into a hole of a cylindrical member;
    b. threading a cap with gas passage means onto said cylindrical member;
    c. placing said cylindrical member and said cap into an ultrasonic solution; and,
    d. placing said cylindrical member and said cap into an autoclave.

5. Process of claim 4 wherein said cylindrical member and said cap provide storage for said dental burr.

* * * * *